United States Patent
Garibaldi (10) Patent No.: US 11,883,385 B2
(45) Date of Patent: Jan. 30, 2024

(54) USE OF A PHOSPHODIESTERASE 10 INHIBITOR FOR THE TREATMENT OF TOURETTE SYNDROME

(71) Applicant: Noema Pharma AG, Basel (CH)

(72) Inventor: George Garibaldi, Basel (CH)

(73) Assignee: Noema Pharma AG, Basel (CH)

( * ) Notice: Subject to any disclaimer, the term of this patent is extended or adjusted under 35 U.S.C. 154(b) by 0 days.

(21) Appl. No.: 18/061,206

(22) Filed: Dec. 2, 2022

(65) Prior Publication Data
US 2023/0149372 A1   May 18, 2023

Related U.S. Application Data

(63) Continuation of application No. PCT/EP2021/065074, filed on Jun. 4, 2021.

(60) Provisional application No. 63/160,302, filed on Mar. 12, 2021, provisional application No. 63/035,310, filed on Jun. 5, 2020.

(51) Int. Cl.
| | |
|---|---|
| *A61K 31/437* | (2006.01) |
| *A61K 9/00* | (2006.01) |
| *A61K 9/48* | (2006.01) |
| *A61K 31/5513* | (2006.01) |
| *A61K 45/06* | (2006.01) |
| *A61K 47/36* | (2006.01) |

(52) U.S. Cl.
CPC .......... *A61K 31/437* (2013.01); *A61K 9/0056* (2013.01); *A61K 9/4808* (2013.01); *A61K 31/5513* (2013.01); *A61K 45/06* (2013.01); *A61K 47/36* (2013.01)

(58) Field of Classification Search
CPC .......................... A61K 31/437; A61K 31/5513
See application file for complete search history.

(56) References Cited

U.S. PATENT DOCUMENTS

| | | | | |
|---|---|---|---|---|
| 5,605,897 A | * | 2/1997 | Beasley, Jr. | ........ A61K 31/5513 514/220 |
| 8,349,824 B2 | | 1/2013 | Flohr et al. | |
| 2003/0032579 A1 | | 2/2003 | Lebel et al. | |
| 2016/0046628 A1 | | 2/2016 | Fantasia et al. | |

FOREIGN PATENT DOCUMENTS

| | | |
|---|---|---|
| EP | 2963037 A1 | 1/2016 |
| WO | WO-2012076430 A1 | 6/2012 |

OTHER PUBLICATIONS

Martino et al., "Systematic Review of Severity Scales and Screening Instruments for Tics: Critique and Recommendations", Movement Disorders, vol. 32, No. 3, pp. 467-478 (2017).*
Bruun et al., "Risperidone as a Treatment for Tourette's Syndrome", Journal of Clinical Psychiatry, vol. 57, No. 1, pp. 29-31 (1996).*
International Search Report and Written Opinion dated Oct. 8, 2021, for International Application No. PCT/EP2021/065074 filed Jun. 4, 2021. (17 pages).

* cited by examiner

Primary Examiner — Kevin E Weddington
(74) Attorney, Agent, or Firm — Goodwin Procter LLP (57) ABSTRACT

Provided herein are methods of treating Tourette Syndrome in a subject in need thereof by administering to the subject compositions comprising a PDE10 inhibitor. Also disclosed are crystalline solid forms of the compound of Formula I and uses thereof:

(I)

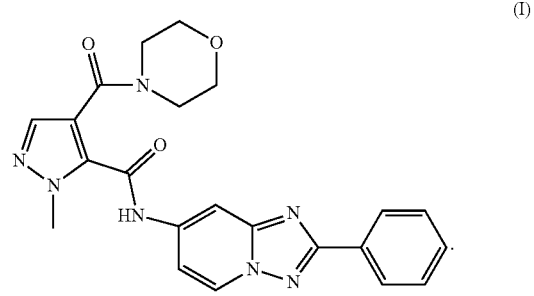

25 Claims, 2 Drawing Sheets

USE OF A PHOSPHODIESTERASE 10 INHIBITOR FOR THE TREATMENT OF TOURETTE SYNDROME

CROSS-REFERENCE TO RELATED APPLICATION

This is a continuation of International Application Number PCT/EP2021/065,074, filed on Jun. 4, 2021, which application claims priority to U.S. Ser. No. 63/035,310 filed on Jun. 5, 2020, and U.S. Ser. No. 63/160,302 filed on Mar. 12, 2021, the contents of each of which is incorporated herein by reference in its entirety.

BACKGROUND

Tourette Syndrome (TS) is a neurologic disorder that is characterized by tics, which are involuntary vocalizations or repetitive, purposeless movements. It is estimated that up to 200,000 Americans have the most severe form of TS, and as many as one in 100 Americans show milder and less complex TS symptoms that may include chronic motor or vocal tics (NIH Handbook on Tourette Syndrome (2012)). The prevalence of TS is estimated to be 0.3% in US children aged 6-17 years, although there are suggestions that this may be an underestimation of its prevalence (Cohen S, et al. Neurosci Biobehav Rev. 37(6): 997-1007 (2013)).

There is currently no medication that is helpful to all patients with TS. While neuroleptic drugs (i.e., antipsychotics) have been effective for treatment of tics in some patients, these medications are associated with significant side effects, and they do not entirely eliminate tic symptoms. In addition, treatment of neurobehavioral disorders associated with TS, such as ADHD, may be complicated as some medications used to treat ADHD are contraindicated in patients with TS (see Prescribing Information for Ritalin) (2013).

Therefore, there is an unmet need to develop new treatments for the spectrum of symptoms of TS, including tics and neurobehavioral disorders.

SUMMARY

In one aspect, provided herein are methods of treating Tourette Syndrome, comprising administering to a subject in need thereof a composition containing a therapeutically effective amount of a therapeutic agent or a pharmaceutically acceptable salt thereof, wherein the therapeutic agent is a compound of Formula I:

(I)

In certain embodiments, the subject has a total tic score of at least 22 on the Yale Global Tic Severity Scale.

In another aspect, provided herein are methods of treating Tourette Syndrome, comprising administering to a subject in need thereof a composition containing a therapeutically effective amount of a therapeutic agent or a pharmaceutically acceptable salt thereof, wherein the subject has a total tic score of at least 22 on the Yale Global Tic Severity Scale and the therapeutic agent is a compound of Formula I:

(I)

In certain embodiments, the subject has previously been administered another therapy for Tourette Syndrome. In certain embodiments, the previous administration of another therapy for Tourette Syndrome is administration of pimozide, haloperidol, or aripiprazole. In certain embodiments, the previous administration of another therapy for Tourette Syndrome is administration of a psychostimulant (e.g., methylphenidate, dextroamphetamine, or lisdexamfetamine) or an alpha 2 adrenergic receptor antagonist (e.g., atipamezole, efaroxan, or idazoxan).

In certain embodiments, administering a therapeutically effective amount of the compound of Formula I, or a pharmaceutically acceptable salt thereof, comprises administering from about 2.5 mg to about 5 mg of the compound of Formula I, or a pharmaceutically acceptable salt thereof. In certain embodiments, the compound of Formula I, or a pharmaceutically acceptable salt thereof, is administered once daily. In certain embodiments, the compound of Formula I, or a pharmaceutically acceptable salt thereof, is administered orally. In certain embodiments, the compound of Formula I, or a pharmaceutically acceptable salt thereof, is administered as a unit dose.

In certain embodiments, the compound of Formula I is administered in free base form. In certain embodiments, the compound of Formula I is administered in the form of a pharmaceutically acceptable salt.

In another aspect, provided herein are methods of treating Tourette Syndrome, comprising administering to a subject in need thereof a composition containing a therapeutically effective amount of a phosphodiesterase 10 (PDE10) inhibitor or a pharmaceutically acceptable salt thereof, wherein the PDE10 inhibitor is a compound of Formula I:

(I)

In certain embodiments, the subject has attention-deficit hyperactivity disorder (ADHD). In certain embodiments, the subject is free of ADHD. In certain embodiments, the subject has obsessive-compulsive disorder (OCD). In certain embodiments, the subject is free of OCD.

Still within the scope of this invention is a solid form of a compound of Formula I:

(I)

wherein the solid form is a crystalline solid of the free base of the compound of Formula I, and the crystalline solid has a melting point by differential scanning calorimetry (DSC) of about 210-214° C. (e.g., about 210° C., about 211° C., about 212° C., about 213° C., or about 214° C.).

Figure 1:
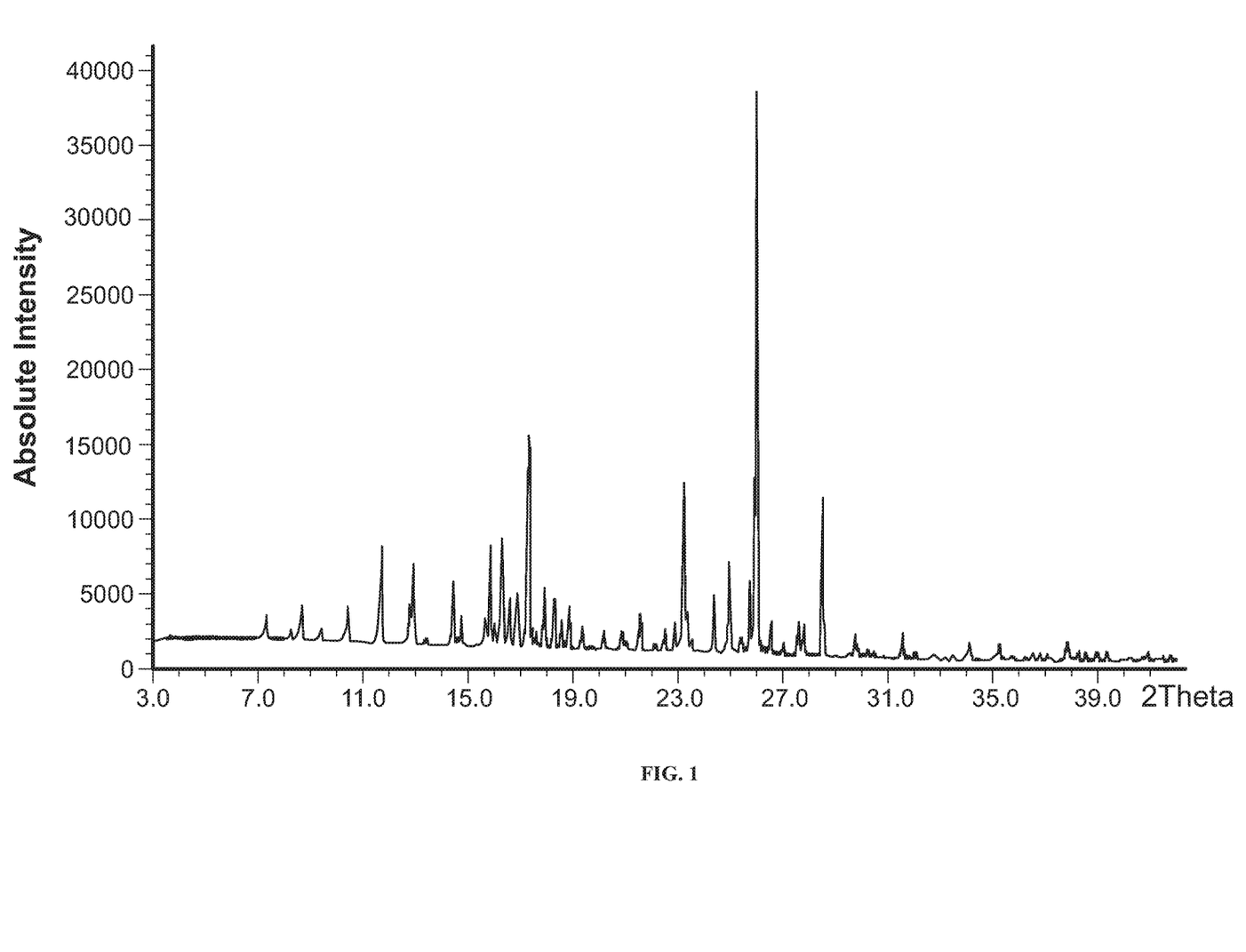
FIG. 1 depicts an exemplary XRPD pattern of a crystalline solid of the free base of the compound of Formula I.

In some embodiments, the above described solid form is a crystalline solid of the free base of Formula I, having an X-ray powder diffraction (XRPD) pattern as substantially shown in FIG. 1.

Figure 2:
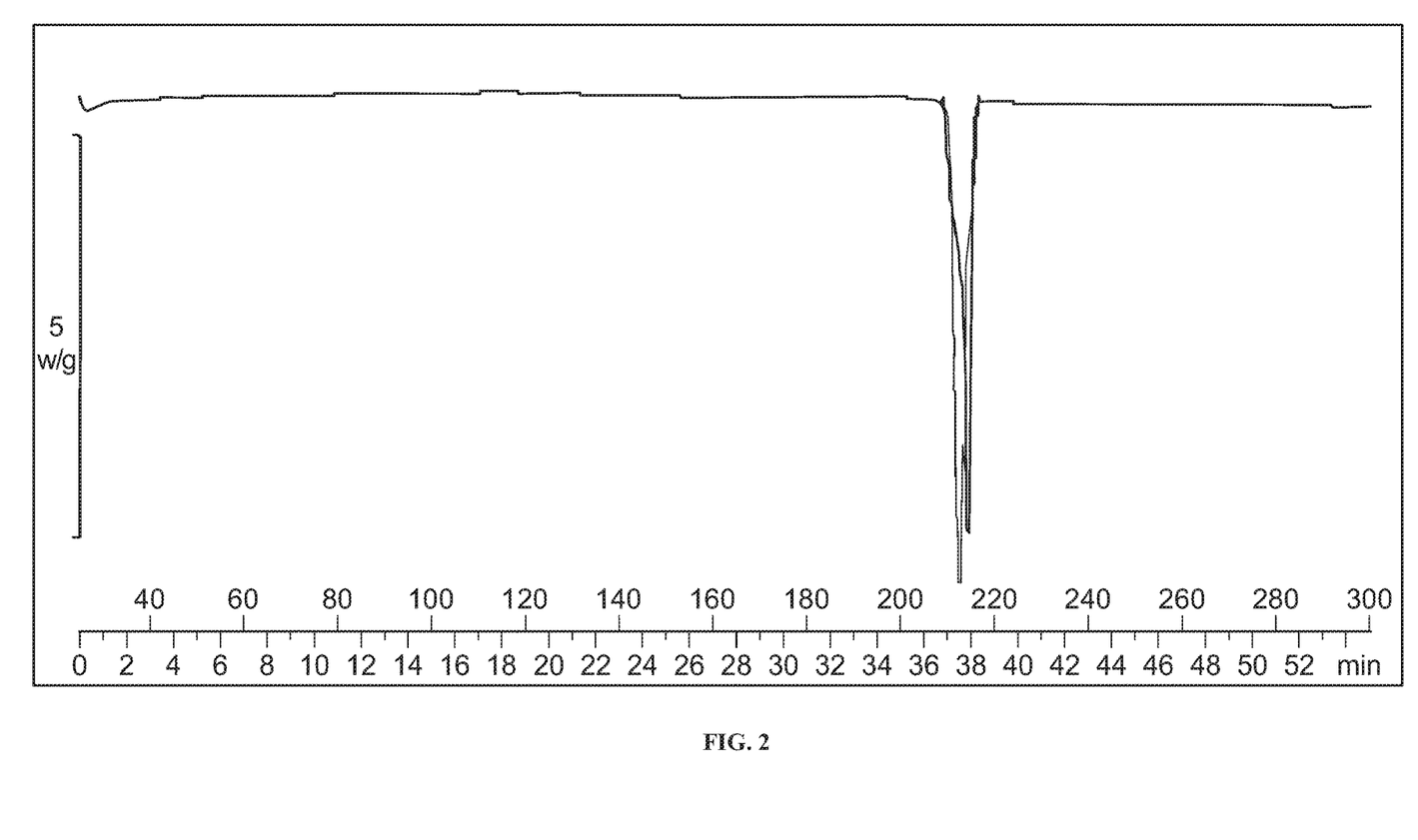
FIG. 2 depicts an exemplary DSC curve of a crystalline solid of the free base of the compound of Formula I.

In some embodiments, the above described solid form is a crystalline solid of the free base of Formula I, having a DSC figure as substantially shown in FIG. 2.

The present invention also covers a method of treating Tourette Syndrome, comprising administering to a subject in need thereof a composition containing a therapeutically effective amount of a crystalline solid of the free base of a compound of Formula I:

(I)

wherein the crystalline solid has a melting point by DSC of about 210-214° C.

In some embodiments, the above described method comprises a crystalline solid of the free base of Formula I, having an X-ray powder diffraction (XRPD) pattern as substantially shown in FIG. 1.

In some embodiments, the above described method comprises a crystalline solid of the free base of Formula I, having a DSC figure as substantially shown in FIG. 2.

DETAILED DESCRIPTION

As generally described herein, the present disclosure provides methods of treating Tourette Syndrome in a subject in need thereof. The present disclosure also describes a crystalline form of the free base of the compound of Formula I, and uses thereof.

Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. The abbreviations used herein have their conventional meaning within the chemical and biological arts. The chemical structures and formulae set forth herein are constructed according to the standard rules of chemical valency known in the chemical arts.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from the group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified. Further, if a variable is not accompanied by a definition, then the previous definition of the variable controls.

As used herein, "pharmaceutical composition" or "pharmaceutical formulation" refers to the combination of an active agent with an excipient or a carrier, inert or active, making the composition especially suitable for diagnostic or therapeutic use in vivo or ex vivo.

"Pharmaceutically acceptable" means approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "pharmaceutically acceptable salt" refers to any salt of an acidic or a basic group that may be present in a compound of the present invention (e.g., the compound of formula (I)), which salt is compatible with pharmaceutical administration.

As is known to those of skill in the art, "salts" of compounds may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds described herein and their pharmaceutically acceptable acid addition salts.

Examples of bases include, but are not limited to, alkali metal (e.g., sodium and potassium) hydroxides, alkaline earth metal (e.g., magnesium and calcium) hydroxides, ammonia, and compounds of formula $NW_4^+$, wherein W is $C_{1-4}$ alkyl, and the like.

Examples of salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $K^+$, $Ca^{2+}$, $NH^{4+}$, and $NW_4^+$ (where W can be a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "pharmaceutically acceptable excipient" refers to a substance that aids the administration of an active agent to and/or absorption by a subject and can be included in the compositions of the present invention without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients, see Martin, Remington's Pharmaceutical Sciences, 15th Ed., Mack Publ. Co., Easton, PA (1975).

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

As used herein, "solid dosage form" means a pharmaceutical dose(s) in solid form, e.g., tablets, capsules, granules, powders, sachets, reconstitutable powders, dry powder inhalers and chewables.

As used herein, "administering" means oral administration, administration as a suppository, topical contact, intravenous administration, parenteral administration, intraperitoneal administration, intramuscular administration, intralesional administration, intrathecal administration, intracranial administration, intranasal administration or subcutaneous administration, transmucosal (e.g., buccal, sublingual, nasal, or transdermal) administration, or the implantation of a slow-release device, e.g., a mini-osmotic pump, to a subject. Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies (e.g., anti-cancer agent, chemotherapeutic, or treatment for a neurodegenerative disease). The compound of Formula I, or a pharmaceutically acceptable salt thereof, can be administered alone or can be co-administered to a subject. Co-administration is meant to include simultaneous or sequential administration of the compound individually or in combination (more than one compound or agent). Thus, the preparations can also be combined, when desired, with other active substances (e.g., to reduce metabolic degradation).

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (e.g., "therapeutic treatment").

The phrase "therapeutically effective amount" as used herein means an amount of a composition (e.g., a composition described herein), or a compound of Formula I, or a pharmaceutically acceptable salt thereof, which is effective for producing some desired therapeutic effect in a subject.

Tourette Syndrome is described in the Diagnostic and Statistical Manual of Mental Disorders, Fifth Edition (DSM-5, 2013) as a disorder characterized by the presence of both multiple motor and one or more vocal tics with Symptoms that have persisted for more than one year. Tics are sudden, rapid, recurrent, nonrhythmic motor movement or vocalization. Typically, symptoms appear before age 18. The term "Tourette Syndrome" as used herein includes each of "persistent (chronic) motor tic disorder," "persistent (chronic) vocal tic disorder," "provisional tic disorder," and "tic disorder." A Tourette Syndrome patient may have both motor and vocal tic symptoms that have been present for at least a year. A patient with a "tic disorder, however, may have only motor or only vocal tics. A patient with "persistent (chronic) motor tic disorder" may have only motor tics. A patient with "persistent (chronic) vocal tic disorder" may have only vocal tics. A patient with "provisional tic disorder" may have symptoms for less than one year.

Patients with TS may also have inattention, hyperactivity, anxiety, mood, and sleep disturbances. Currently, TS may be diagnosed using one or more rating scales. An exemplary rating scale is the Yale Global Tic Severity Scale, as described in Storch et al., Psychol Assess., 2005, 17(4):486-91.

Compound

The compound of Formula I, as depicted below, is a phosphodiesterase 10 (PDE10) inhibitor, also known as 1-methyl-4-(morpholine-4-carbonyl)-N-(2-phenyl[1,2,4]triazolo[1,5-a]pyridin-7-yl)-1H-pyrazole-5-carboxamide.

(I)

A method of chemically synthesizing the compound of Formula I (including Example 1 provided herein, infra) is described in U.S. Pat. No. 8,349,824, which is incorporated by reference in its entirety.

In various embodiments, the pharmaceutically acceptable salt of the compound of Formula I can be a salt of the compound of Formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

This invention also covers a solid form of a compound of Formula I:

(I)

wherein the solid form is a crystalline solid of the free base of the compound of Formula I, and the crystalline solid has a melting point by differential scanning calorimetry (DSC) of about 210-214° C. (e.g., about 210° C., about 211° C., about 212° C., about 213° C., or about 214° C.).

In some embodiments, the above described solid form is a crystalline solid of the free base of Formula I, having an X-ray powder diffraction (XRPD) pattern as substantially shown in FIG. 1.

In some embodiments, the above described solid form is a crystalline solid of the free base of Formula I, having a DSC figure as substantially shown in FIG. 2.

Pharmaceutical Compositions

In one aspect, provided herein is a pharmaceutical composition comprising the compound of Formula I, or a pharmaceutically acceptable salt thereof, and a pharmaceutically acceptable excipient, for the treatment of Tourette Syndrome in a subject in need thereof. It should be understood that the compound of Formula I as described herein includes the crystalline solid of the free base of the compound of Formula I as described herein.

In various embodiments, the amount of the compound of Formula I, or a pharmaceutically acceptable salt thereof, in the pharmaceutical compositions described herein can be from about 1 mg to about 10 mg, about 1.5 mg to about 10 mg, about 2 mg to about 10 mg, about 2.5 mg to about 10 mg, about 3 mg to about 10 mg, about 3.5 mg to about 10 mg, about 4 mg to about 10 mg, about 4.5 mg to about 10 mg, about 5 mg to about 10 mg, about 6 mg to about 10 mg, about 7 mg to about 10 mg, about 8 mg to about 10 mg, about 9 mg to about 10 mg, about 1 mg to about 9 mg, about 1 mg to about 8 mg, about 1 mg to about 7 mg, about 1 mg to about 6 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, about 1 mg to about 1.5 mg, about 1.5 mg to about 9 mg, about 1.5 mg to about 8 mg, about 1.5 mg to about 7 mg, about 1.5 mg to about 6 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, about 1.5 mg to about 2 mg, about 2 mg to about 9 mg, about 2 mg to about 8 mg, about 2 mg to about 7 mg, about 2 mg to about 6 mg, about 2 mg to about 5 mg, about 2 mg to about 4.5 mg, about 2 mg to about 4 mg, about 2 mg to about 3.5 mg, about 2 mg to about 3 mg, about 2 mg to about 2.5 mg, about 2.5 mg to about 9 mg, about 2.5 mg to about 8 mg, about 2.5 mg to about 7 mg, about 2.5 mg to about 6 mg, about 2.5 mg to about 5 mg, about 2.5 mg to about 4.5 mg, about 2.5 mg to about 4 mg, about 2.5 mg to about 3.5 mg, about 2.5 mg to about 3 mg, about 3 mg to about 9 mg, about 3 mg to about 8 mg, about 3 mg to about 7 mg, about 3 mg to about 6 mg, about 3 mg to about 5 mg, about 3 mg to about 4.5 mg, about 3 mg to about 4 mg, about 3 mg to about 3.5 mg, about 3.5 mg to about 9 mg, about 3.5 mg to about 8 mg, about 3.5 mg to about 7 mg, about 3.5 mg to about 6 mg, about 3.5 mg to about 5 mg, about 3.5 mg to about 4.5 mg, about 3.5 mg to about 4 mg, about 4 mg to about 9 mg, about 4 mg to about 8 mg, about 4 mg to about 7 mg, about 4 mg to about 6 mg, about 4 mg to about 5 mg, about 4 mg to about 4.5 mg, about 4.5 mg to about 9 mg, about 4.5 mg to about 8 mg, about 4.5 mg to about 7 mg, about 4.5 mg to about 6 mg, about 4.5 mg to about 5 mg, about 5 mg to about 9 mg, about 5 mg to about 8 mg, about 5 mg to about 7 mg, about 5 mg to about 6 mg, about 6 mg to about 9 mg, about 6 mg to about 8 mg, about 6 mg to about 7 mg, about 7 mg to about 9 mg, about 7 mg to about 8 mg, or about 8 mg to about 9 mg. In certain embodiments, the amount of the compound of Formula I, or a pharmaceutically acceptable salt thereof, in the pharmaceutical compositions described herein can be from about 2.5 mg to about 5 mg.

In various embodiments, the amount of the compound of Formula I, or a pharmaceutically acceptable salt thereof, in the pharmaceutical compositions described herein can be about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg. In certain embodiments, the amount of the compound of Formula I, or a pharmaceutically acceptable salt thereof, in the pharmaceutical compositions described herein can be about 2.5 mg. In certain embodiments, the amount of the compound of Formula I, or a pharmaceutically acceptable salt thereof, in the pharmaceutical compositions described herein can be about 5 mg.

In another aspect, provided herein is a pharmaceutical composition comprising from about 2.5 mg to about 5 mg of the compound of Formula I, or a pharmaceutically acceptable salt thereof; and a pharmaceutically acceptable excipient, for the treatment of Tourette Syndrome in a subject in need thereof. In another aspect, provided herein is a pharmaceutical composition comprising from about 5 mg to about 15 mg of the compound of Formula I, or a pharmaceutically acceptable salt thereof and a pharmaceutically acceptable excipient, for the treatment of Tourette Syndrome in a subject in need thereof.

In another aspect, provided herein is a pharmaceutical composition comprising from about 2.5 mg to about 5 mg of the compound of Formula I, or a pharmaceutically acceptable salt thereof; and a pharmaceutically acceptable excipient, for the treatment Tourette Syndrome in a subject in need thereof, wherein the subject has a total tic score of at least 22 on the Yale Global Tic Severity Scale.

In various embodiments, for effective treatment Tourette Syndrome in a subject in need thereof, wherein the subject has a total tic score of at least 22 on the Yale Global Tic Severity Scale, the compound of Formula I, or a pharmaceutically acceptable salt thereof, in a pharmaceutical composition can be administered in a daily dosage from about 1 mg to about 20 mg, about 2 mg to about 19 mg, about 3 mg to about 18 mg, about 4 mg to about 17 mg, about 5 mg to about 16 mg, about 5 mg to about 15 mg, about 6 mg to about 14 mg, about 7 mg to about 13 mg, about 8 mg to about 12 mg, about 9 mg to about 11 mg, or about 9 mg to about 10 mg. In certain embodiments, the amount of the daily dosing can be from about 2.5 mg to about 5 mg. In certain embodiments, the amount of the daily dosing can be from about 5 mg to about 15 mg.

In various embodiments, for effective treatment Tourette Syndrome in a subject in need thereof, wherein the subject has a total tic score of at least 22 on the Yale Global Tic Severity Scale, the compound of Formula I, or a pharmaceutically acceptable salt thereof, in a pharmaceutical composition can be administered in a daily dosage of about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg. In certain embodiments, the amount of the daily dosing can be about 2.5 mg, about 3 mg, about 3.5 mg, about 4 mg, about 4.5 mg, or about 5 mg. In certain embodiments, the amount of the daily dosing can be about 5 mg, about 7.5 mg, about 10 mg, about 12.5 mg, or about 15 mg.

In various embodiments, the pharmaceutical compositions described herein comprise a therapeutically effective amount of the free base form of the compound of Formula I.

In various embodiments, the pharmaceutical compositions described herein comprise a therapeutically effective amount of a pharmaceutically acceptable salt of the compound of Formula I. In some embodiments, the pharmaceutically acceptable salt of the compound of Formula I can be a salt of the compound of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration. In certain embodiments, the pharmaceutical compositions disclosed herein are administered orally.

The pharmaceutical compositions provided herein may also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions provided herein may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. In various embodiments, the pharmaceutical dosage forms described herein can be administered as a unit dose. Typical unit dosage forms include prefilled, premeasured ampules or syringes of the liquid compositions or pills, tablets, capsules or the like in the case of solid compositions.

In various embodiments, the pharmaceutical compositions provided herein are administered to the patient as a solid dosage form. In certain embodiments, the solid dosage form is a capsule. In certain embodiments, the solid dosage form is a tablet.

In various embodiments, the pharmaceutical compositions provided herein comprise the compound of Formula I as the sole active agent, or in combination with other active agents.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Methods of Use and Treatment

In one aspect, provided herein are methods of treating Tourette Syndrome in a subject in need thereof.

In various embodiments, provided herein are methods for treating Tourette Syndrome in a subject in need thereof, comprising administering to a subject in need thereof a composition containing a therapeutically effective amount of a therapeutic agent or a pharmaceutically acceptable salt thereof, wherein the therapeutic agent is a compound of Formula I:

In certain embodiments, the subject has a total tic score of at least 18, at least 19, at least 20, at least 21, at least 22, at least 23, at least 24, or at least 25 on the Yale Global Tic Severity Scale. In certain embodiments, the subject has a total tic score of at least 22 on the Yale Global Tic Severity Scale.

In some embodiments, provided herein are methods of treating Tourette Syndrome in a subject in need thereof, comprising administering to a subject in need thereof a composition containing a therapeutically effective amount of a therapeutic agent or a pharmaceutically acceptable salt thereof, wherein the subject has a total tic score of at least 22 on the Yale Global Tic Severity Scale and the therapeutic agent is a compound of Formula I:

In various embodiments, the subject has previously been administered another therapy for Tourette Syndrome. In certain embodiments, the previous administration of another therapy for Tourette Syndrome is administration of pimozide, haloperidol, or aripiprazole. In certain embodiments, the previous administration of another therapy for Tourette Syndrome is administration of a psychostimulant (e.g., methylphenidate, dextroamphetamine, or lisdexamfetamine) or an alpha 2 adrenergic receptor antagonist (e.g., atipamezole, efaroxan, or idazoxan). In certain embodiments, the previous administration of another therapy for Tourette Syndrome is administration of pimozide, haloperidol, aripiprazole, methylphenidate, dextroamphetamine, lisdexamfetamine, atipamezole, efaroxan, or idazoxan.

In various embodiments, administering a therapeutically effective amount of the compound of Formula I, or a pharmaceutically acceptable salt thereof, comprises administering a composition having an amount of the compound as described herein, supra.

In various embodiments, the composition comprises the compound of Formula I, or a pharmaceutically acceptable salt thereof, as the sole active agent.

In various embodiments, the composition comprises the compound of Formula I, or a pharmaceutically acceptable salt thereof, in combination with another active agent. In certain embodiments, the other active agent is olanzapine or risperidone.

In various embodiments, the composition comprises inactive agents selected from the group consisting of mannitol, microcrystalline cellulose, sodium starch glycolate, sucrose monopalmitate, hydroxypropyl methylcellulose, colloidal silicon dioxide, and sodium stearyl fumarate.

In various embodiments, administering comprises administering the compound of Formula I, or a pharmaceutically acceptable salt thereof, in a capsule.

In various embodiments, the capsule shell consists of gelatine, titanium dioxide, red iron oxide, and yellow iron oxide.

In various embodiments, the capsule described above comprises about 1 mg to about 10 mg of the compound of Formula I, or a pharmaceutically acceptable salt thereof.

In various embodiments, the capsule comprises about 2.5 mg to about 5 mg of the compound of Formula I, or a pharmaceutically acceptable salt thereof.

In various embodiments, administering comprises administering the compound of Formula I, or a pharmaceutically acceptable salt thereof, in an amount of about 2.5 mg to about 5 mg once daily.

In various embodiments, administering comprises administering the compound of Formula I, or a pharmaceutically acceptable salt thereof, in an amount of about 5 mg to about 15 mg once daily.

In various embodiments, administering comprises administering the compound of Formula I, or a pharmaceutically acceptable salt thereof, in an amount of about 1 mg to about 20 mg once daily.

In various embodiments, administering comprises administering the compound of Formula I, or a pharmaceutically acceptable salt thereof, in an amount of about 5 mg, about 7.5 mg, about 10 mg, about 12.5 mg, or about 15 mg once daily.

In various embodiments, administering comprises administering the compound of Formula I, or a pharmaceutically acceptable salt thereof, in an amount of about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, or about 20 mg once daily. In embodiments, administering comprises administering the compound of Formula I, or a pharmaceutically acceptable salt thereof, in an amount of about 2.5 mg once daily. In embodiments, administering comprises administering the compound of Formula I, or a pharmaceutically acceptable salt thereof, in an amount of about 5 mg once daily. In various embodiments, administering comprises administering the compound of Formula I, or a pharmaceutically acceptable salt thereof, in an immediate release formulation.

In various embodiments, administering comprises administering the compound of Formula I, or a pharmaceutically acceptable salt thereof, in an extended release formulation.

In various embodiments, administering maintains efficacy throughout the day.

In various embodiments, the compound of Formula I, or a pharmaceutically acceptable salt thereof, is administered once, twice, three, four, or five times daily. In certain embodiments, the compound of Formula I, or a pharmaceutically acceptable salt thereof, is administered once daily.

In various embodiments, the compound of Formula I, or a pharmaceutically acceptable salt thereof, is administered orally.

In various embodiments, the compound of Formula I, or a pharmaceutically acceptable salt thereof, is administered as a unit dose.

In various embodiments, the compound of Formula I is administered in free base form.

In various embodiments, the compound of Formula I is administered in the form of a pharmaceutically acceptable salt. In certain embodiments, the pharmaceutically acceptable salt of the compound of Formula I can be a salt of the compound of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. In certain embodiments, the compound of Formula I is administered in a crystalline form.

In various embodiments, provided herein are methods of treating Tourette Syndrome in a subject in need thereof, comprising administering to a subject in need thereof a composition containing a therapeutically effective amount of a phosphodiesterase 10 (PDE10) inhibitor or a pharmaceutically acceptable salt thereof, wherein the PDE10 inhibitor is a compound of Formula I:

(I)

In various embodiments, the TS subject has also been diagnosed with one or more diseases, disorders, or conditions selected from the group consisting of attention-deficit hyperactivity disorder (ADHD), compulsive disorder (OCD), oppositional defiant disorder (ODD), conduct disorder, anxiety disorder, autism, a mood disorder, a phobia, and depression. In various embodiments, the TS subject does not have ADHD, OCD, ODD, conduct disorder, anxiety disorder, autism, a mood disorder, a phobia, and depression. In certain embodiments, the subject has ADHD. In certain embodiments, the subject is free of ADHD. In certain embodiments, the subject has OCD. In certain embodiments, the subject is free of OCD.

In various embodiments, the compound of Formula I is administered as a monotherapy.

In various embodiments, the methods provided herein further comprise administering a therapeutically effective amount of a second therapeutic agent to the subject.

Without further elaboration, it is believed that one skilled in the art can, based on the above description, utilize the present invention to its fullest extent. The following specific examples are therefore to be construed as merely illustrative, and not limitative of the remainder of the disclosure in any way whatsoever.

EXAMPLES

In order that the disclosure described herein may be more fully understood, the following examples are set forth. The examples described in this application are offered to illustrate the compounds, pharmaceutical compositions, and methods provided herein and are not to be construed in any way as limiting their scope.

Example 1: Synthesis of 1-methyl-4-(morpholine-4-carbonyl)-N-(2-phenyl[1,2,4]triazolo[1,5-a]pyridin-7-yl)-1H-pyrazole-5-carboxamide (Compound of Formula I) [See U.S. Pat. No. 8,349,824]

1-methyl-5-(2-phenyl-[1,2,4]triazolo[1,5-a]pyridin-7-ylcarbamoyl)-1H-pyrazole-4-carboxylic acid methyl ester Step A—1,2-diamino-4-bromo-pyridinium2,4,6-trimethyl-benzenesulfonate: to a cooled suspension of O-(mesitylsulfonyl)hydroxylamine (11.22 g, 52.1 mmol, 1 eq) in dichloromethane (130 ml) was portionwise added 4-bromopyridin-2-amine (9.3 g, 52.1 mmol, 1 eq.) (exothermic reaction, some cooling is needed) giving a white suspension. After 1 hour the white suspension was diluted with diethyl ether (120 ml). The white solid was collected by filtration, washed with diethyl ether and dried affording 1,2-diamino-4-bromo-pyridinium 2,4,6-trimethyl-benzenesulfonate (16.74 g, 82.7%) as white crystals. mp.: 176-180° C. MS: m/z=188.2, 190.2 (M+H+).

Step B—7-bromo-2-phenyl-[1,2,4]triazolo[1,5-a]pyridine: 1,2-Diamino-4-bromopyridinium 2,4,6-trimethylbenzenesulfonate (15.6 g, 40.2 mmole) in pyridine (106 ml) was heated overnight at 100° C., with benzoyl chloride (9.4 nil, 80 mmole) giving a redbrown solution and after 2 hrs a brown suspension. The reaction mixture was concentrated in vacuo and the residue was triturated for 2.5 hr in saturated aqueous ammonium chloride solution (300 ml), while neutralizing to pH 6-7 with saturated aqueous sodium bicarbonate solution. The solid was collected by filtration, washed with water (40 ml) and dried affording 7-bromo-2-phenyl-[1,2,4]triazolo[1,5-a]pyridine (6.78 g, 61.6%) as an off-white solid. mp.: 189-191° C. MS: m/z=276.1, 274.2 (M+H+).

Step C—(2-phenyl-[1,2,4]triazolor[1,5-a]pyridin-7-yl)-carbamic acid tert-butyl ester: to an nitrogen purged suspension of 7-bromo-2-phenyl-[1,2,4]triazolo[1,5-a]pyridine (9 g, 32.8 mmol) in dioxane (180 ml) was added successively tert-butyl carbamate (4.71 g, 39.4 mmol), tris(dibenzylidene-acetone)dipalladium(0) (601 mg, 657 μmol), 4,5-bis(diphenylphos-phino)-9,9-dimethylxanthene (760 mg, 1.31 mmol) and cesium carbonate (15 g, 46 mmol). The brown mixture was then stirred for 22 hours at 100° C., under nitrogen atmosphere. The solvent was removed in vacuo and the brown residue partitioned between ethyl acetate and water. The aqueous layer was extracted twice with ethyl acetate and the combined organic layers were washed with water (3×120 ml) and with brine and dried with magnesium sulfate. The solution was concentrated in vacuo to ca 80 ml: crystallization. The suspension was stirred for 10 min in an ice bath and the solid was collected by filtration, washed with little cold ethyl acetate and dried affording (2-phenyl-[1,2,4]triazolo[1,5-a]pyridin-7-yl)-carbamic acid tert-butyl ester (7.09 g) as an off-white solid. The mother liquor was evaporated and the residue (4.79 g) loaded on silica (16 g). The product was isolated by chromatography on a 120 g silica cartridge (eluent heptane/ethyl acetate 10-50%, 45 min) yielding a second crop of 1.748 g of a white solid. mp.: 200-201° C. dec. MS: m/z=311.3 (M+H+). Total yield: 86.7%.

Step D—2-phenyl-[1,2,4]triazolo[1,5-a]pyridin-7-ylamine: a suspension of (2-phenyl-[1,2,4]triazolo[1,5-a]pyridin-7-vi)-carbamic acid test-butyl ester (8.5 g, 27.4 mmol) in hydrochloric acid (6 N in diethyl ether, 175 ml) was stirred overnight at room temperature. The suspension was diluted under roofing with water (ca 21) and ethyl acetate, the aqueous layer was washed once with ethyl acetate, made alkaline with 32% aqueous sodium hydroxide and extracted twice with ethyl acetate. The combined organic layers were dried with magnesium sulfate and the solvent was removed in vacuo affording 2-phenyl-[1,2,4]triazolo[1,5-a]pyridin-7-ylamine (5.52 g, 95.9%) as a light pink solid. mp.: 212-213° C. MS: 211.2 (M+H+).

Step E—1-methyl-5-(2-phenyl-[1,2,4]triazolo[1,5-a]pyridin-7-ylcarbamoyl)-1H-pyrazole-4-carboxylic acid methyl ester: a solution of 2-phenyl-[1,2,4]triazolo[1,5-a]pyridin-7-ylamine (1.534 g, 7.3 mmol), 4-(methoxycarbonyl)-1-methyl-1H-pyrazole-5-carboxylic acid (1.61 g, 8.76 mmol) propylphosphonic anhydride (50% in ethyl acetate, 10.7 ml, 18.2 mmol) and diisopropylethylamine (5.1 ml, 29.2 mmol) in tetrahydrofurane (54 ml) was stirred at 70° C., for 1.25 hr giving a white suspension. The cooled suspension was poured in saturated aqueous sodium bicarbonate solution (200 ml), stirred at room temperature for 15 min. and the solid was collected by filtration, washed with water and dried affording 1-methyl-5-(2-phenyl-[1,2,4]triazolo[1,5-a]pyridin-7-ylcarbamoyl)-1H-pyrazole-4-carboxylic acid methyl ester (2.5% g, 94.5%) as a white solid. mp.: 243-7° C. MS: m/z 377.2 (M+H+).

1-Methyl-5-(2-phenyl-[1,2,4]triazolo[1,5-a]pyridin-7-ylcarbamoyl)-1H-pyrazole-4-carboxylic acid A white suspension of 1-methyl-5-(2-phenyl-[1,2,4]triazolo[1,5-a]pyridin-7-ylcarbamoyl)-1H-pyrazole-4-carboxylic acid methyl ester (2.37 g, 6.3 mmol) and lithium hydroxide monohydrate (291 mg, 6.93 mmol) in methanol (100 ml) and water (20 ml) was stirred for 1.25 hr at 70° C., giving after 20 min a colorless solution. The methanol was removed in vacuo, the residue was diluted with water and the cooled aqueous solution was neutralized with 2N aqueous hydrochloric acid (3.46 ml, 6.03 mmol). The solid was collected by filtration and dried affording 1-methyl-5-(2-phenyl-[1,2,4]triazolo[1,5-a]pyridin-7-ylcarbamoyl)-1H-pyrazole-4-carboxylic acid (2.21 g, 97%) as a white solid. mp.: >300° C. MS: m/z=361.1 (M+H+).

1-methyl-4-(morpholine-4-carbonyl)-N-(2-phenyl[1,2,4]triazolo[1,5-c]pyridin-7-yl)-1H-pyrazole-5-carboxamide A mixture of 1-methyl-5-(2-phenyl-[1,2,4]-triazolo[1,5-a]pyridin-7-ylcarbamoyl)-1H-pyrazole-4-carboxylic acid (100 mg, 276 mol), morpholine (240 μl, 2.76 mmol) and propylphosphonic anhydride (50% in ethyl acetate, 407 μl, 690 umol) in tetrahydrofurane (7 ml) was stirred for 3 hours at 70° C. The mixture was diluted with ethyl acetate and washed with saturated aqueous sodium hydrogencarbonate solution and brine. The organic layer was separated, dried with magnesium sulfate and the solvent evaporated. The residue (76 mg white foam) was triturated with diethylether and ethyl acetate affording 1-methyl-4-(morpholine-4-carbonyl)-N-(2-phenyl-[1,2,4]triazolo[1.5-a]pyridin-7-yl)-1H-pyrazole-5-carboxamide (53 mg, 44.5%) as a white solid. mp.: 203-207° C. MS: m/Z=432.4 (M+H").

Example 2: A Study of the Efficacy of the Compound of Formula I for the Treatment of Subjects with Tourette Syndrome Objectives of Study Primary Efficacy Objective: evaluate the efficacy of a double-blind, 12-week, once daily dose of the compound of Formula I (2.5 mg to 5 mg) compared with a placebo in adolescent and adult patients with Tourette Syndrome (TS). The primary outcome is the change from the baseline to week 12 (or endpoint) in the Yale Global Tic Severity Scale (YGTTS).

Secondary Objectives:
1. The percentage change from baseline to week 12 (or endpoint) in YGTSS total tic scores (TTS); the efficacy is assessed by the percentage subject changes of TTS from randomization to the last visit (Week 12) on the YGTSS.
2. The response rate on the investigator-rated Tourette Syndrome-Clinical Global Impression (TS-CGI) Change scale; the response rate (the percentage of patients with a score of 1 or 2) is assessed by TS-CGI Change scale at Week 12 (or endpoint) with a reference to baseline.
3. The response rate on the Patient Global Impression of Change (PGIC); the patient-reported response (the percentage of patients with a score of 1 or 2) is reported at study Week 12 (or endpoint).
4. The partial remission rate on the investigator-rated TS-CGI Improvement scale; the partial remission rate (the percentage of patients with a score of 3) is assessed by TS-CGI Improvement scale from baseline to week 12 (or endpoint).
5. The changes from baseline to week 12 (or endpoint) in TS-CGI Severity scale scores; this is assessed by the change from baseline to week 12 (or endpoint) on the TS-CGI Severity scale scores.

Study Design

This was a multi-center, randomized, double-blind, placebo-controlled study in patients who exhibited evidence of suboptimal benefit from their current treatment.

Patients, who were diagnosed with TS, signed the informed consent, mey the study the eligibility criteria, and agreed to participate in the study, entered a screening period of up to 30 days.

Eligible patients were randomized via interactive voice/web response system to receive one of two treatments:
1. Treatment A: 2.5 mg or 5 mg dose of the compound of Formula I
2. Treatment B: placebo At the end of the screening period, patients who continued to meet all entry criteria were randomized to receive double blind treatment.

Study Phases

The total study duration was up to 16 weeks.
1. Screening and stabilization phase: 4 weeks
2. Randomized Phase: 12 weeks Number of Patients A total of 90 patients were randomized to treatment. It was estimated that 120 patients were screened to randomize 90 eligible patients.

Target Population

Patients met the following criteria for study entry:
1. An ability and willingness to provide written informed consent and to comply with the study procedures;
2. Fluency in the language of the investigator, study staff, and the informed consent.
3. Be aged between 11 and 50 years old;
4. The subject meets the current Diagnostic and Statistical Manual of Mental Disorders, Fifth Edition (DSM-5) diagnostic criteria for TS and requires drug therapy;
5. The subject has a TTS≥22 on the YGTSS at baseline visit; and
6. For female patients, agreement to use two adequate methods of contraception, including at least one barrier method of contraception and at least one method of contraception with a failure rate of <1% per year, from the start of screening until 90 days after the last dose of the study drug.

Patients who met any of the following criteria were excluded from study participation:
1. Females who have a positive pregnancy test result or who are pregnant or breast-feeding;
2. Subjects who have secondary tic symptoms accompanied by late-onset tics, Huntington's chorea, neuroacanthocytosis, mental retardation, or autism;
3. Subjects who have comorbidities requiring drug therapy, such as attention deficit/attention-deficit hyperactivity, obsessive-compulsive disorder, or oppositional defiant disorder (if a case is judged by the investigator that drug therapy is not required for any of the above diseases during this study, then the patient is eligible to participate in this trial);
4. Subjects who have lower intelligence;
5. Subjects who have a current diagnosis of bipolar disorder, mental disorder, schizophrenia, or depressive disorder;
6. Subjects who have experienced episodes of epileptic seizure in the past year;
7. Subjects who have a history of severe traumatic brain injury or stroke;
8. Subjects who have any unstable medical conditions or are currently ill (e.g., congenital heart disease, arrhythmia or cancer), which, in the investigator's judgment, will put them at a risk of major adverse event during this trial, or will interfere with safety and efficacy assessments;
9. Subjects who require both drug therapy and cognitive-behavioral therapy (CBT, including habitual inversion therapy, cognitive therapy, relaxation training, etc.) during the trial period; or
10. Subjects who have participated in any clinical trial of any investigational therapy within the past one month.

Efficacy Outcome Measures

The primary outcome was the change from baseline to week 12 (or endpoint) in the Yale Global Tic Severity Scale (YGTTS).

The secondary efficacy outcome measures for this study were as follows:
1. Percentage change from Baseline to Week 12 (or endpoint) in YGTSS TTS; the efficacy is assessed by the percentage subject changes of total tic scores (TTS) from randomization to the last visit (Week 12) on the Yale Global Tic Severity Scale (YGTSS).

2. Response rate on TS-CGI Improvement scale; the response rate (the percentage of patients with a score of 1 or 2) is assessed by TS-CGI Improvement scale from Baseline to Week 12 (or endpoint).
3. Response rate on the Patient Global Impression of Change (PGIC); the patient-reported response (the percentage of patients with a score of 1 or 2) is reported at study Week 12 (or endpoint).
4. Partial remission rate on TS-CGI Improvement; the partial remission rate (the percentage of patients with a score of 3) is assessed by TS-CGI Improvement scale from Baseline to Week 12 (or endpoint).
5. Changes from baseline to week 12 (or endpoint) in TS-CGI Severity scale scores; the efficacy is assessed by changes from Baseline to Week 12 (or endpoint) in TS-CGI Severity scale scores Safety Outcome Measures The safety outcome measures for the study were:
1. Incidence, nature and severity of adverse events
2. Lab test results, vital signs assessment, and ECG parameters Schedule of Assessments

TABLE 1

Schedule of Assessments

| Visit | Screening | Baseline | Week 2 | Week 4 | Week 8 | Week 12 | EP |
|---|---|---|---|---|---|---|---|
| Informed consent | X | | | | | | |
| Eligibility/Demographics/Medical History | X | | | | | | |
| Vital Signs | | X | X | X | X | X | X |
| Physical/Neurological examination | X | X | X | X | X | X | X |
| YGTTS | X | X | X | X | X | X | X |
| CGI-C | | Clinical notes | x | X | X | X | X |
| PGI-C | | Self-recorded observation | X | X | X | X | X |
| CGI-S | X | X | X | X | X | X | X |
| Sheehan Disability Scale | | X | | | | X | X |
| ECG | X | | | | | | X |
| LABS | X | | | | | | X |
| Urine pregnancy | X | X | X | X | X | X | X |
| C-SSRS | X | X | X | X | X | X | X |
| Urine drug test | X | X | | | As needed | | X |
| Adverse events | | X | X | X | X | X | X |
| Concomitant medications | X | X | X | X | X | X | X |

Objectives and Endpoints

Primary and Secondary Objectives and Endpoints are listed in Table 2 below:

TABLE 2

Primary and Secondary Objectives and Endpoints

| Objectives | Endpoints |
|---|---|
| Primary | |
| To identify the optimal dose range of the compound of Formula I associated with tic control in adult patients with TS. | "Response" as rated by the Tourette Syndrome Clinical Global Impression of Change (TS-CGI-C) at week 12 or Post Treatment. Response is defined as a rating of "Minimally improved "Much improved" and "Very much improved" |
| Secondary | |
| To evaluate safety and tolerability of the compound of Formula I | Incidence and severity of adverse events. Laboratory and cardiovascular safety will be also evaluated |
| To evaluate the change in TS symptom severity | Change from Baseline to Week 12 (or Post Treatment) in YGTSS of the total tic scores (TTS) of the Yale Global Tic Severity Scale (YGTSS) |
| To evaluate the patient reported Clinical Global Impression of Change (PGI-C) | Assessed by TS-CGI Severity (TS-CGI-S)scale from Baseline to Week 12 (or Post Treatment) Patient-reported Clinical Global |

Example 3: A Study of the Safety and Efficacy of the Compound of Formula I for the Treatment of Subjects with Tourette Syndrome Provided below was an open-label, Phase IIa, multi-center, 12-week prospective study to evaluate the safety and efficacy of the compound of Formula I at a daily dose range of 5 mg to 15 mg in adult male patients with Tourette Syndrome (TS).

TABLE 2-continued

Primary and Secondary Objectives and Endpoints

| Objectives | Endpoints |
| --- | --- |
| To evaluate the patient reported rating of the Medication Satisfaction Questionnaire (MSQ) | Impression of Change (PGI-C) as completed by patients from Baseline to Week 12 (or Post Treatment) Patient reported rating of the Medication Satisfaction Questionnaire (MSQ) from Baseline to Week 12 (or Post Treatment) |

Study Design

This was an open-label, multi-centre, Phase IIa study to identify the optimal dose of the compound of Formula I in adult male patients with TS that would elicit an anti-tic response as rated by the Tourette Syndrome Clinical Global Impression of change (TS-CGI-C) at week 12 or post-treatment. Response was defined as a rating of "Minimally Improved", "Much improved" and "Very much improved".

A total of 10 patients were enrolled into this study. Male adult patients who show evidence of suboptimal benefit from their current treatment were enrolled in this study.

Potential patients underwent a screening assessment. Eligible patients were assigned a starting dose of 5 mg once daily. Treatment continued for a maximum of 12 weeks or until unacceptable intolerance or patient withdrawal of consent. Dose escalation was allowed at the investigator's discretion, in increments of 2.5 mg, up to a maximum of 15 mg once daily. During the study, if intolerance occurs at any given dose, the daily dose of the compound were reduced by 2.5 mg.

Screening assessments, clinical efficacy and safety assessments and patient reported outcomes were performed according to the Schedule of Activities (SoA) (Table 3 below).

Response to treatment were rated by the Tourette Syndrome Clinical Global Impression of Change (TS-CGI-C) at week 12 or end of treatment. Response was defined as a rating of "Minimally improved", "Much improved" and "Very much improved". Secondary efficacy evaluations included the total tic scores (TTS) of the Yale Global Tic Severity Scale (YGTSS) and illness severity rated on the TS-CGI Severity (TS-CGI-S). Safety were assessed by physical examination, vital signs, ECG, laboratory assessment, adverse events and serious adverse events monitoring. Patient reported outcomes were assessed by the Clinical Global Impression of Change (PGI-C) and the Medication Satisfaction Questionnaire (MSQ).

Study Treatment

Study treatment was defined as any investigational intervention(s), marketed product(s), placebo, or medical device(s) intended to be administered to a patient according to the study protocol.

Study Treatment(s) administered are shown in Table 4 below:

TABLE 4

| Study Treatment | |
| --- | --- |
| Treatment Name | Compound of Formula I |
| Type | Drug |
| Dose Formulation | Capsule |
| Unit Dose Strength(s) | 2.5 mg, 5.0 mg |
| Dosage Level(s) | Once daily |
| Route of Administration | Oral |

Preparation/Handling/Storage/Accountability: The clinical formulation of the compound of Formula I is a reddish-brown hard gelatine capsule for oral administration. The capsule fill consists of the compound of Formula I and the

TABLE 3

Schedule of Activities

| | SCREENING | STUDY TREATMENT Weeks 1-12 | | | POST TREATMENT |
| --- | --- | --- | --- | --- | --- |
| | Screening Up to 4 weeks | Week 4 | Week 8 | Week 12/End of Treatment[2] | 28 days after fast dose |
| Informed consent | X | | | | |
| Eligibility/Demographics/Medical History (including IO) | X | | | | |
| Physical/Neurological/examination | X | | | X | X |
| Clinical assessment | | X[1,3] | | X[1,3] | X |
| YGTTS | X | X[4] | X[4] | X | |
| TS-CGI-S | X | X[4] | X[4] | X | |
| TS-CGI-C | Clinical notes | X[4] | X[4] | X | |
| PGI-C | Self-recording | | | X | |
| Medication Questionnaire Satisfaction | | | | X | |
| ECG | X | | | X | X |
| Labs | X | | | X | X |
| Vital signs | X | as required[3] | | X | |
| C-SSRS | X | | | X | |
| Urine drug test | X | as required[3] | | X | |
| Adverse Events | X | X | | X | X |
| Concomitant medications | X | X | | X | X |

[1]Patient fails to complete 12-week treatment period or withdraw from the study
[2]Conducted by telephone at the discretion of the investigator. Based on investigator assessment, dose may be in increased or decreased in 2.5 mg increments
[3]Conducted Weeks 1 to 11 inclusive at investigator discretion and judgement
[4]Clinic visit inactive ingredients mannitol, microcrystalline cellulose, sodium starch glycolate, sucrose monopalmitate, hydroxypropyl methylcellulose, colloidal silicon dioxide, and sodium stearyl fumarate.

The capsule shell consists of gelatine, titanium dioxide, red iron oxide and yellow iron oxide. All excipients used in the formulation are compendial (Ph. Eur. and/or USP/NF) grade.

Hard gelatin capsules are available containing 2.5 mg and 5 mg of the compound of Formula I. Capsules of the compound are stored under the recommended storage conditions "Store at 15-25° C.", "Protect from light and moisture."

Example 4: A Crystalline Form of Compound of Formula I

Preparation of Crystalline Form: Amorphous form of the compound of Formula I was stirred in water or a mixture of 50% water in methanol at 65° C. for 3 days to afford a crystalline form of the free base of the compound of Formula I. The crystalline form is thermodynamically stable at least between 20° C. and 60° C. The XRPD and DSC graphs were as substantially shown in FIGS. 1 and 2. The XRPD pattern can be obtained by following protocols known in the field.

Melting Point: The maximal melting point peak ($T_m$) of the crystalline form was determined using DSC, which was performed using a Mettler Toledo DSC 821e with Sample Robot TSO 801RO. A sample of 2-5 mg was placed in AL-crucibles 40 uL with AL-piercing lids and the sample was heated at a rate of 10° C./min from 25° C. to 300° C. Temperatures at crystalline melting peak start, peak onset, peak max, and peak end were collected. DSC shows the $T_m$ of the crystalline form was 213.16° C.

Solubility: The above crystalline form showed a very low solubility in aqueous solutions at pH>3 (<0.004 mg/mL). Solubility in simulated gastric fluid (SGF), fasted state simulated intestinal fluid (FaSSIF), and fed state simulated intestinal fluid (FeSSIF) was 0.019 mg/ml, 0.006 mg/mL, and 0.022 mg/mL, respectively. Solubility increased 50-100-fold in the presence of surfactants (e.g., Tween-80, sodium dodecyl sulfate, dioctyl sulfosuccinate, or Pluronic F68) and cyclodextrins; however it was still rather low. Overall, the crystalline exhibited a poor solubility at ambient temperature (22° C.) not only in aqueous systems, but also in most of the tested organic solvents (<50 mg/mL).

Stability: Preliminary forced degradation study of the crystalline form of the free base of the compound of Formula I in acidic, basic, oxidative, and photolytic stress conditions was conducted to investigate the viability of the crystalline form in various stress conditions. Since the solubility of the compound of Formula I was low in the standard solvent ethanol, ethanol was replaced by N-methyl-2-pyrrolidone (NMP).

A defined amount of the crystalline form of the free base of the compound of Formula I (0.2-0.8 mg) was weighed into a 1.8 mL HPLC vial and stored open (75% RH) or closed (ambient) at the temperature and the time indicated. After incubation, compound was dissolved in 1-1.5 mL NMP to a final concentration of 0.2-0.5 mg/mL and submitted to UPLC analysis (254 nm). The results are as substantially shown in Table 5 below. The data show that the crystalline form was stable at various temperatures in solid state (<0.5% degradation products), e.g., stable for at least 4 weeks at 40-60° C.

TABLE 5

| Preliminary Solid State Stability | |
|---|---|
| Storage condition | UPLC analysis (Area % main peak) |
| 4 w, 40° C. | 100 |
| 4 w 60° C. | 100 |
| 4 w, 40° C., 75% RH | 100 |
| 4 w, RT | 100 |
| 4 w, 4° C. | 100 |
| 1 h, 80° C. | 100 |
| 1 d, 80° C. | 100 |
| 8 d, 80° C. | 100 |

The crystalline form of the free base of the compound of Formula I was stable for up to 8 days in solid state at 80° C. and in solution at pH 3 to pH 7 at RT. At higher or lower pH, degradation was observed. The crystalline form was stable after exposure to light in solid state. In solution, it was stable towards daylight and, time dependent, moderately stable to unstable in the Suntest. It was also stable towards oxidation for 1 day, but showed some sensitivity upon prolonged exposure. The crystalline form was compatible with almost all excipients; however drug recovery in the CompaS assay strongly depended on the solvent used for extraction.

In the suspension vehicle used for PK, PD, and Tox studies (0.5% HPC/1% Tween 80), The crystalline form was also stable for up to 5 weeks at RT, with only minor particle growth and no hydrate formation. For parenteral administration, a 30% Kleptose formulation (1.5 mg/ml, physiologic osmolality, pH 6.2), with a stability of at least 4 weeks at 40° C. was developed.

INCORPORATION BY REFERENCE

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating Tourette Syndrome, comprising administering to a subject in need thereof a composition comprising a therapeutically effective amount of a first therapeutic agent, wherein the therapeutic agent is a compound of Formula I:

or a pharmaceutically acceptable salt thereof.

2. The method of claim 1, wherein the subject has a total tic score of at least 22 on the Yale Global Tic Severity Scale at the start of treatment.

3. The method of claim 1, wherein therapeutic efficacy of the treatment is determined by assessing improvement based on the Tourette Syndrome Clinical Global Impression of Change (TS-CGI-C) scale.

4. The method of claim 1, wherein therapeutic efficacy of the treatment is determined by assessing improvement based on the Tourette Syndrome Clinical Global Impression of Change (TS-CGI-C) scale, and the subject is determined to be minimally improved.

5. The method of claim 1, wherein therapeutic efficacy of the treatment is determined by assessing improvement based on the Tourette Syndrome Clinical Global Impression of Change (TS-CGI-C) scale, and the subject is determined to be much improved.

6. The method of claim 1, wherein therapeutic efficacy of the treatment is determined by assessing improvement based on the Tourette Syndrome Clinical Global Impression of Change (TS-CGI-C) scale, and the subject is determined to be very much improved.

7. The method of claim 1, wherein therapeutic efficacy of the treatment is determined by assessing improvement based on the Yale Global Tic Severity Scale.

8. The method of claim 1, wherein therapeutic efficacy of the treatment is determined by assessing improvement based on the Yale Global Tic Severity Scale, where the subject shows a change from baseline.

9. The method of claim 1, wherein therapeutic efficacy of the treatment is determined by assessing improvement based on the Yale Global Tic Severity Scale, where the subject shows a change from baseline to week 12.

10. The method of claim 1, wherein therapeutic efficacy of the treatment is determined by assessing improvement based on the Patient-reported Clinical Global Impression of Change (PGI-C) scale.

11. The method of claim 1, wherein therapeutic efficacy of the treatment is determined by assessing improvement based on the Patient-reported Clinical Global Impression of Change (PGI-C) scale, and the subject shows an improvement from baseline.

12. The method of claim 1, wherein therapeutic efficacy of the treatment is determined by assessing improvement based on the Medication Satisfaction Questionnaire (MSQ).

13. The method of claim 1, wherein administering of the therapeutic is once daily.

14. The method of claim 1, wherein administering of the therapeutic is oral administration.

15. The method of claim 1, wherein administering of the therapeutic is as a unit dose.

16. The method of claim 1, wherein administering of the therapeutic comprises administering the therapeutic in an amount of about 2.5 mg to about 10 mg.

17. The method of claim 1, wherein administering is in an amount of about 2 mg to about 10 mg.

18. The method of claim 1, wherein administering comprises administering the therapeutic in an amount of about 5 mg to about 15 mg.

19. The method of claim 1, wherein administering comprises administering the compound of Formula I, or a pharmaceutically acceptable salt thereof in an amount selected from the group consisting of about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, 18.5 mg, about 19 mg, about 19.5 mg, and about 20 mg.

20. The method of claim 1, wherein the therapeutic is in its free base form.

21. The method of claim 1, wherein said therapeutic is the pharmaceutically acceptable salt.

22. The method of claim 1, wherein the composition comprises inactive agents selected from the group consisting of mannitol, microcrystalline cellulose, sodium starch glycolate, sucrose monopalmitate, hydroxypropyl methylcellulose, colloidal silicon dioxide, and sodium stearyl fumarate.

23. The method of claim 1, wherein the composition is in a capsule.

24. The method of claim 1, wherein the composition is in an immediate release formulation.

25. The method of claim 1, wherein the composition is in an extended release formulation.

* * * * *